United States Patent [19]
Fleury et al.

[11] Patent Number: 5,594,251
[45] Date of Patent: Jan. 14, 1997

[54] GAMMA CAMERA WITH ROTATING ARM

[75] Inventors: Christophe J. M. Fleury, Guyancourt; Bertrand Legue, Paris, both of France

[73] Assignee: Sopha Medical, Paris, France

[21] Appl. No.: 382,570

[22] Filed: Feb. 2, 1995

[30] Foreign Application Priority Data

Feb. 2, 1994 [FR] France .................................. 94 01166

[51] Int. Cl.⁶ ................................................. G01T 1/166
[52] U.S. Cl. ............................ 250/363.05; 250/363.08
[58] Field of Search ........................... 250/363.05, 363.08

[56] References Cited

U.S. PATENT DOCUMENTS

| | | | |
|---|---|---|---|
| 4,220,861 | 9/1980 | Columbo et al. | 250/363.05 |
| 4,223,222 | 9/1980 | Gray et al. | |
| 4,476,389 | 10/1984 | Ueyama et al. | 250/363.05 |
| 5,262,648 | 11/1993 | Stark | 250/363.05 |
| 5,367,169 | 11/1994 | Pierfitte | 250/363.05 |

FOREIGN PATENT DOCUMENTS 517602  12/1992  European Pat. Off.

OTHER PUBLICATIONS

Patent Abstracts of Japan, vol. 7, No. 109 (P-196) 12 May 1983 JP-A-58 030 685 (Tokyo Shibaura Denki K. K.) Feb. 23, 1983, abstract.

*Primary Examiner*—Carolyn E. Fields
*Attorney, Agent, or Firm*—Kerkam, Stowell, Kondracki & Clarke, P.C.; Edward J. Kondracki

[57] ABSTRACT

A gamma camera has a base fixed to a frame along a substantially horizontal axis of rotation called the axis of rotation of the gamma camera, bearing at least one arm that is substantially parallel to the axis of rotation and provided, at its free end, with a detector head. The arm is rotationally movable about an axis called an axis of angulation of the detector head, substantially parallel to the axis of rotation of the gamma camera, and passing through the position at which said arm is fixed to the base. In one embodiment, the axis of angulation of the detector head is offset with respect to an axis of orientation of the head toward the head detection surface and passes substantially through the center of gravity formed by the arm and the head. In another embodiment, the end of the arm holding the head has a two-finger gripping piece with bevelled ends.

34 Claims, 2 Drawing Sheets

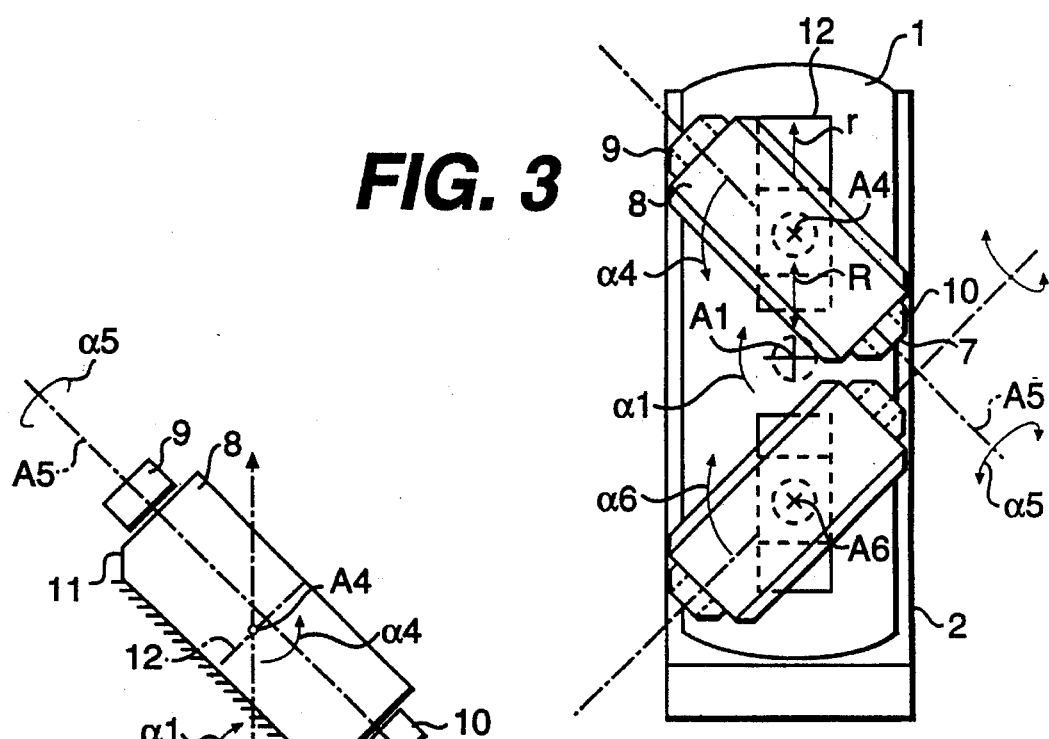
FIG. 3
FIG. 5
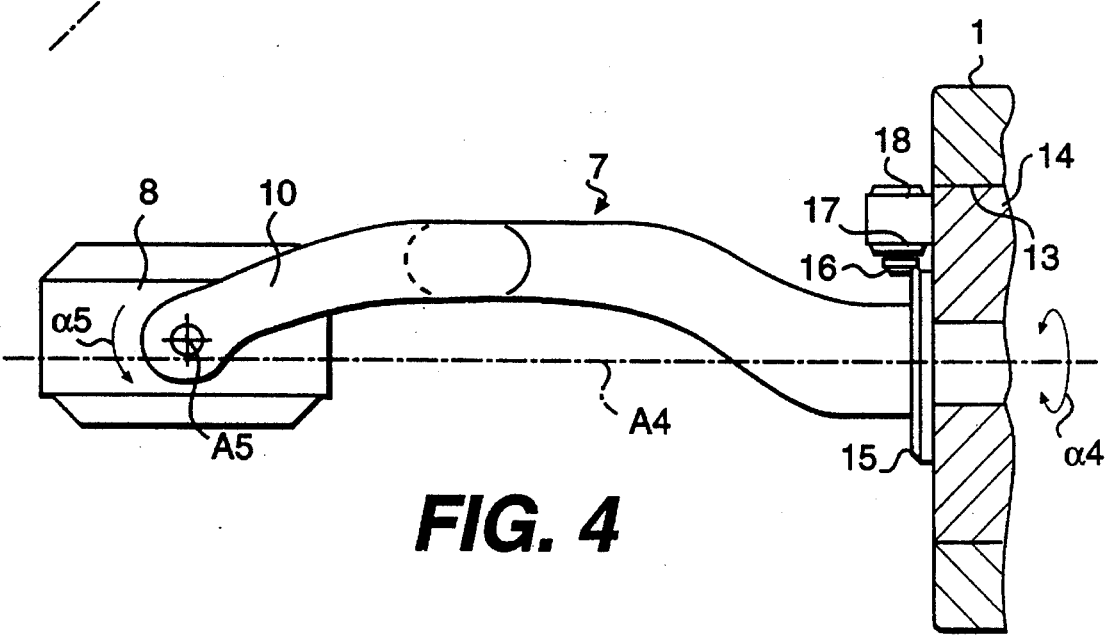
FIG. 4

GAMMA CAMERA WITH ROTATING ARM

BACKGROUND OF THE INVENTION

1. Field of the Invention

The present invention relates to the field of gamma cameras and, more particularly, to the field of gamma cameras comprising two detector heads capable of carrying out tomographic examinations.

A gamma camera is an apparatus comprising a base that is fixed or movable with respect to the ground and having at least one arm provided, at its free end, with a detector. This detector has an array of photomultiplier tubes whose input faces, which are juxtaposed with one another, cover the detection surface of the detector head and determine its field of detection.

2. Description of the Prior Art

The principle of the examination is as follows. A radioactive substance is injected into a patient to be examined. The gamma radiation produced by the radioactive emission that emanates from this patient goes through a collimator and excites a scintillator crystal of the detector which converts the energy of the gamma photons into a light energy that is detectable by the photomultiplier tubes. These photomultipliers then produce electrical signals depending on the light intensity received.

By carrying out operations of barycentric localization on all these electrical signals it is possible, in a known way, to determine the X, Y coordinates of the scintillation in the field of detection. An incremental acquisition is then made by totalizing the number of scintillations detected throughout the field of detection.

Thus, by leaving the detector head in a given position for a certain time above the body examined, it is possible, for a given viewing angle, to obtain an image that reveals the concentration of radioactive substance in the body.

It has become the common practice to use a rotating base. It is possible then to make tomographic examinations that consist in acquiring one image per viewing angle for a large number of viewing angles, evenly spaced out over an angular sector of at least 180°. The image of an examined volume is then reconstituted with computation algorithms.

In order to improve the sensitivity, gamma cameras with rotating bases having two detector heads instead of only one have been brought into use, these detector heads being positioned before each other, either face to face or, preferably at a fixed angle, preferably equal to 90° with respect to each other. Furthermore, a device commonly called a hoist or elevator has been used, enabling the arms to move away from each other or to approach each other so as to bring the detector heads as close as possible to the patient's body.

FIG. 1 illustrates a gamma camera comprising the above-mentioned different improvements. It is provided with two arms, fixed horizontally to a vertical base 1 that is itself fixed to a frame 2. For obvious reasons of symmetry, only the upper arm, referenced 3 in figure 1, shall be described. This arm 3 holds a detector head 4 at its free end, by means of a U-shaped stirrup 5.

The base 1 rotates about an axis A1 which is conventionally the rotational axis of the gamma camera.

Each detector head 4 is fixed to the stirrup 5 rotationally about an axis A2 passing substantially through the center of said head and perpendicularly to the axis A1. The axis A2 is called, by convention, the axis of orientation of the detector head.

Furthermore, each of these detector heads 4 is fixed rotationally about an axis A3 that is perpendicular to the axis A2 and passes through two bearings fixing the detector head 4 to the stirrup 5. The axis A3 is called, by convention, the axis of "angulation" of the detector head.

Furthermore, each arm 3 can carry out a radial translational motion along the rotating base in a radial translational direction R so as to approach or move away from the axis of rotation A1, within the limits of a window 6. The translational motions of the two arms are preferably symmetrical. The windows 6 are furthermore closed by the sliding of a system of telescopic curtains.

Hence, many positions of the detector heads 4 are possible. Each position is defined by a set of coordinates (r, α1, α2, α3) where r is a radial translation of the arms along R, α1 is an angle of rotation of the gamma camera along A1, α2 is an angle of orientation of the detector head considered along A2 and α3 is an angle of angulation of this very same head along A3.

The complex functions that the stirrup 5 has to perform need to be emphasized.

This stirrup 5 must first of all hold the detector head 4 in a totally reliable manner. It must then enable, firstly, the orientation of the detector heads 4 and, secondly, their angulation.

In order to carry out these different functions, the arm 3 supports the stirrup 5 at a single point, located substantially at the center of the horizontal part of said stirrup 5. Furthermore, the vertical uprights of the U forming the stirrup 5 have a height that is great enough to enable the obtaining of an angulation of the detector heads 4 by an angle α3 at least equal to 90° without the edges of said heads 4 coming into contact with the above-mentioned horizontal part.

Furthermore, because of the height of the vertical uprights of the stirrup 5, the arm 3 is curved so that its end fixed to the base 1 is close enough to the axis of rotation A1 of the gamma camera. Nevertheless, the arm 3 is then longer, and it needs to be solidly joined to the base 1.

The present invention is aimed at proposing a gamma camera that overcomes the above-mentioned drawbacks and makes it possible, in particular, to obtain a structure that is simplified but capable of bearing a greater, hence heavier, head, eliminating the stirrup of the prior art without thereby in any way eliminating the above-mentioned different functions of translation and rotation, this camera being particularly reliable and also very attractive as regards cost.

SUMMARY OF THE INVENTION

This aim, as well as others that shall appear here below, are achieved by means of a gamma camera comprising a base, fixed to a frame that is fixed or movable along a substantially horizontal axis of rotation called the axis of rotation of the gamma camera, bearing at least one arm that is substantially parallel to the axis of rotation and provided, at its free end, with a detector head, wherein the arm is rotationally movable about an axis called an axis of angulation of the detector head, substantially parallel to the axis of rotation of the gamma camera, and passing through the position at which said arm is fixed to the base.

BRIEF DESCRIPTION OF THE DRAWINGS

The following description, which has no restrictive character, will provide for a clearer understanding of the way in which the invention may be put into practice.

It must be read with reference to the appended drawings, of which:

FIG. 3 shows a front view of a gamma camera according to the invention;

FIG. 4 shows a side view of an arm of a gamma camera according to the invention;

FIG. 5 shows a front view of the detector heads of a gamma camera according to the invention, in a relative position where they form an angle of 90° with respect to each other.

DESCRIPTION OF THE PREFERRED EMBODIMENTS

Figure 1:
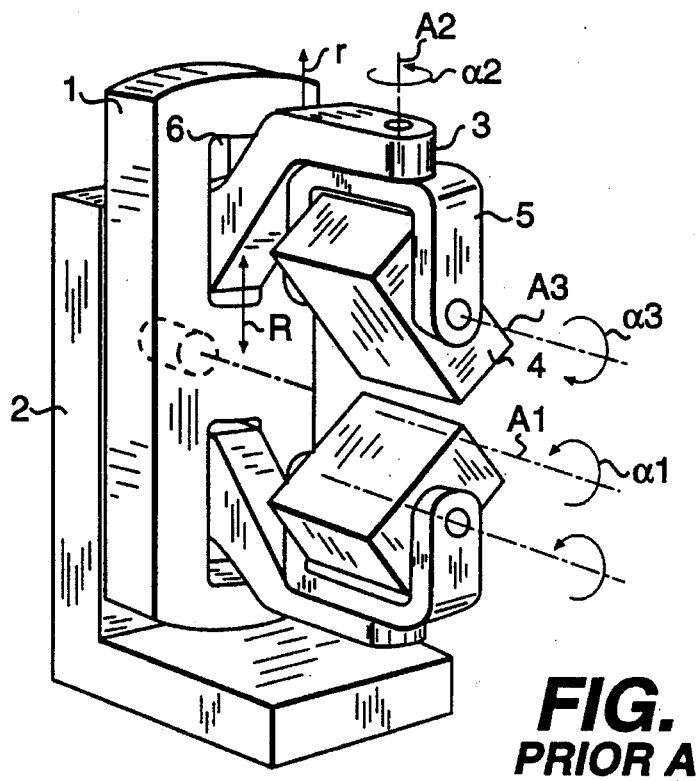
FIG. 1 shows a view in perspective of a gamma camera according to the prior art.

Since FIG. 1 has been described in the above preamble, it shall not be re-examined here. However, it forms an integral part of the description, especially as regards the elements common with those of the gamma camera of the invention.

Figure 2:
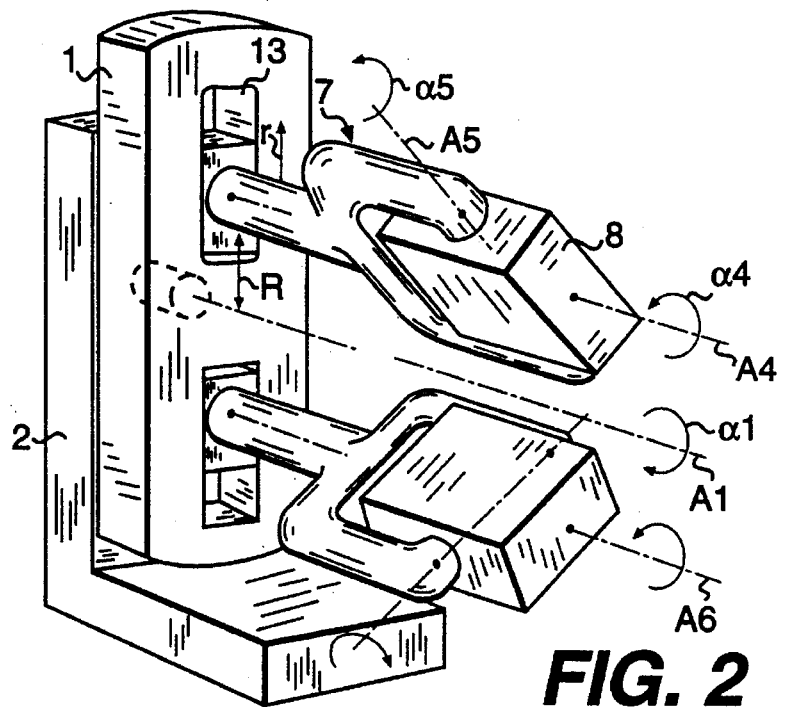
FIG. 2 shows a view in perspective of a gamma camera according to the invention.

FIG. 2 shows a gamma camera of the invention comprising a base 1 fixed to a frame 2 according to an axis of rotation A1 called an axis of rotation of the gamma camera.

The frame 2 has a general shape of an L while the base 1 has the approximate shape of a rectangular parallelepiped. The base 1 is fixed rotationally to the frame 2, at the middle of the vertical upright of the L of this frame. As indicated in FIG. 3, the axis A1 is horizontal and goes through the base 1 in the vicinity of its center.

The base 1 bears, by means of a bearing, at least one arm 7 provided, at its free end, with a detector head 8. In the figures, the base 1 has two substantially horizontal arms. These arms are rotationally fixed to the base 1, on either side of the axis A1, symmetrically.

Similarly, since the arrangements of the different elements borne by these arms are similarly symmetrical with respect to the axis A1, care will be taken here below to describe only one arm, the arm referenced 7 in FIGS. 2, 3 and 4, which comprises the detector head referenced 8.

The arm 7 is fixed to the base 1 so as to be rotationally movable about an axis A4 called an axis of angulation of the detector head 8. An axis A6 is an axis of angulation of the detector head symmetrical with the head 8. As indicated by FIG. 3, the axes A4 and A6 are substantially parallel to the axis A1 and are advantageously in one and the same plane as this axis A1.

As illustrated by FIG. 4, the arm 7 advantageously has a generally curved shape, forming an arc whose chord would be the axis A4. The curvature of the arm 7 makes it possible to obtain a clear space between the detector head 8 and the base 1 so that a patient can have a certain degree of freedom, especially in order to throw his or her arms backwards, which happens during certain examinations. The length of the arm 7 is in the range of 1.20 meters. This arrangement makes it possible to balance the angulation motion of the head 8 and of the arm 7. The deflection of the curvature is of the order of 30 cm.

The free end of the arm 7 forms a two-fingered gripping piece divided into two parts or fingers 9, 10, spaced out like the prongs of a fork.

The detector head 8 has a weight of about 400 Kg. It has a detection surface whose dimensions, namely length ×width, are in the range of 420×540 mm. It is held at the terminal parts of the two fingers in an axis of rotation A5 called an axis of orientation of the detector head. As is illustrated in FIG. 3, when the head is rotated in angulation along α4, the axis A5 remains contained in a plane (that of the figure) which is substantially perpendicular to the axes A1 and A4. The axis A4 goes through the middle of two bearings that fix the detector heads 8 to the fingers of the arm 7.

FIG. 5 shows a front view of the detector heads 8 of the gamma camera of the invention in a relative position of 90° with respect to each other. In this position, as well as also in other positions that are not shown in the present application, the field of detection of the gamma camera should be maximal. Now, owing to the impossibility of placing the photomultiplier tubes right against the casing of the detector head, the useful detection field does not occupy the overall surface area of the head. This results in a dead zone, present in the detectable space, when the two heads are attached to each other. A patient's body cannot be placed in this dead zone which would not contribute to the reconstructed image. Consequently, the dead zone, namely the hatched zone 11 which does not face the detection surface of the two detector head assemblies, should be reduced and minimal. To this end, the end of the finger 10, as well as the end of the finger that corresponds to it in the other arm, have been bevelled. Thus, in the above-mentioned 90° position, the detection surfaces are as close to each other as possible. The part of the casing located close to the surface of the head is also bevelled.

Furthermore, FIG. 5 shows that the axis A4 is not positioned perpendicularly to the axis A5. It is only orthogonal to it. Indeed, the axis A4 is advantageously offset, with respect to the alignment with the axis A5, towards the detection surface of the head 8. In this position, the axis A4 passes substantially through the center of gravity of the assembly formed by the arm 7 and the head 8. This offset of the axis A4, equal in one example to about 78 mm, helps compensate for a major shift of the center of gravity 12 of the detector heads 8 towards their detection surface due to the presence of the collimator placed on these detection surfaces. Through this positioning of the axis A4, the angulation of the arm 7 will be facilitated, for the balance of the arm-head assembly will be more achieved with greater precision. Consequently, the energy expended as well as the vibrations and/or the variations in speed in the angulation of the heads 8 and the rotation of the arms 7 will be thereby limited.

Furthermore, the gamma camera of the invention has what is called an elevator, enabling the arms to move closer to each other or away from each other, symmetrically with respect to the axis A1, within the limits of windows 13 made in a cladding of the base 1, according to a motion R of radial translation. The elevator is a mechanical chain-operated system forming a carrousel that rotates between two end pinions. These chains move a carriage vertically for each arm, this carriage being referenced 14 in FIG. 4.

The arm 7 is fixed to the carriage 14 by any means, notably by screws not shown in the figures. The carriage 14 rises or descends along rails, under the effect of a shifting of the chains. The chains are driven by a motor of the base 1 (not shown).

It must be noted that the functions of angulation of the arm 7 and of radial translation of the arm 7 must be independent of each other.

In order to achieve this aim, a toothed wheel 15 (FIG. 4) is fixedly joined to the base of the arm 7. The base of the arm is held in a bearing borne by the carriage 14. This toothed wheel 15 is engaged in a pinion 16 that is orthogonal to it. This pinion 16 is itself connected to a shaft 17 of a electrical geared motor unit 18 borne by the carriage 14. The geared motor unit 18 drives the pinion 16 rotationally irrespectively of the radial position r of the arm 7. The toothed wheel 15 is fixed to the arm 7 and rotates, quite like said arm, at an angle of angulation α4 about the axis A4.

Hence, with the gamma camera of the invention, there is a possibility of achieving all the positions needed for the different examinations, whether tomographic or otherwise, by the angulation of the arm itself and, of course, by the rotation of the base and the orientations of the detector heads. By coupling the different possibilities of rotation of angles α1, α4 and α5 with the translation r along R, a position is reached that is any position (r, α1, α2, α3) while, at the same time, the problems of the prior art are resolved.

What is claimed is:

1. A gamma camera comprising a frame, a base rotationally fixed to the frame along a substantially horizontal axis of rotation of the gamma camera, said base having an arm supported thereto at one end to extend substantially parallel to the axis of rotation of the gamma camera and supporting at a free end thereof a first detector head, said arm being rotationally movable about an axis of angulation of the first detector head, said arm being disposed substantially parallel to the axis of rotation of the gamma camera and said axis of angulation passing through a first position at which said one end of the arm is supported to the base, and further wherein the axis of angulation of the first detector head is offset with respect to the axis of orientation of the first detector head towards a detection surface of said first detector head and passes substantially through the center of gravity formed by said one arm and said first detector head.

2. A gamma camera according to claim 1, wherein said axis of orientation is contained in a plane substantially orthogonal to the axis of angulation of the first detector head and passes through a position at which said first detector head is supported to the arm.

3. A gamma camera according to claim 2, wherein said arm is movable according to a movement of radial translation along the base so as to approach or move away from the axis of rotation of the gamma camera.

4. A gamma camera according to claim 2, wherein said arm is curved in a manner which defines an arc and provides a space between the first detector head that the arm supports and the base.

5. A gamma camera according to claim 1, wherein said arm is movable according to a movement of radial translation along the base so as to approach or move away from the axis of rotation of the gamma camera.

6. A gamma camera according to claim 1, wherein the arm is curved in a manner which defines an arc and provides a space between the first detector head that the arm supports and the base.

7. A gamma camera according to claim 1, wherein the end of the arm is a two-finger gripping piece that grips the first detector head between the two fingers.

8. A gamma camera according to claim 7, wherein the fingers have bevelled ends.

9. A gamma camera according to claim 1, wherein the arm is fixed to a carriage on the base and wherein a geared motor unit supported by said carriage rotatably drives said arm in angulation.

10. A gamma camera according to claim 1, including a second arm supported at one end to said base to extend substantially parallel to the axis of rotation of the gamma camera and having a free end supporting a second detector head, said second arm being rotationally movable about an axis of angulation of the second detector head, said second arm being substantially parallel to the axis of rotation of the gamma camera and said axis of angulation of the second detector head passing through a second position at which said one end of the second arm is supported to the base.

11. A gamma camera according to claim 10, wherein the second detector head is rotationally movable about a second axis called an axis of orientation of the second detector head, said second axis of orientation being contained in a plane substantially orthogonal to the axis of angulation of the second detector head and passing through a second position at which said second detector head is supported to the second arm.

12. A gamma camera according to claim 11, wherein the second axis of angulation of the second detector head is offset with respect to the axis of orientation of the second detector head towards a detection surface of said second head and passes substantially through the center of gravity formed by the second arm and the second head.

13. A gamma camera according to claim 10, wherein the second arm is movable according to a movement of radial translation along the base so as to approach or move away from the axis of rotation of the gamma camera.

14. A gamma camera according to claim 16, wherein the first arm and second arm are curved in a manner which defines an arc and provides a space between each of the associated first and second detector heads and the base.

15. The gamma camera according to claim 10, wherein the ends of each of the first and second arms comprise a two-finger gripping piece adapted to grip an associated detector head.

16. A gamma camera according to claim 15, wherein the ends of the fingers of each gripping piece are bevelled.

17. A gamma camera according to claim 10, wherein each of the first and second arms is fixed to a carriage on the base and wherein a geared motor unit supported by said carriage rotatably drives said first and second arms in angulation.

18. A gamma camera comprising a frame, a base rotationally fixed to the frame along a substantially horizontal axis of rotation of the gamma camera, said base having a first arm supported thereto at one end to extend substantially parallel to the axis of rotation of the gamma camera and supporting at a free end thereof a first detector head, said first arm being rotationally movable about an axis of angulation of the first detector head, said first arm being disposed substantially parallel to the axis of rotation of the gamma camera and said axis of angulation passing through a first position at which said one end of the first arm is supported to the base, said gamma camera further including a second arm supported at one end to said base to extend substantially parallel to the axis of rotation of the gamma camera and having a free end supporting a second detector head, said second arm being rotationally movable about an axis of angulation of the second detector head, said second arm being substantially parallel to the axis of rotation of the gamma camera and said axis of angulation of the second detector head passing through a second position at which said one end of the second arm is supported to the base, and further wherein the ends of each of the first and second arms comprise a two-finger gripping piece adapted to grip an associated detector head and at least one finger of the two-finger gripping piece has bevelled ends.

19. A gamma camera according to claim 18, wherein the first detector head is rotationally movable about a first axis called an axis of orientation of the first detector head, said axis of orientation being contained in a plane substantially orthogonal to the axis of angulation of the first detector head and passing through a position at which said first detector head is supported to the first arm.

20. A gamma camera according to claim 19, wherein the axis of angulation of the first detector head is offset with respect to the axis of orientation of the first detector head towards a detection surface of said first detector head and passes substantially through the center of gravity formed by said first arm and the first detector head.

21. A gamma camera according to claim 20, wherein said first arm is movable according to a movement of radial translation along the base so as to approach or move away from the axis of rotation of the gamma camera.

22. A gamma camera according to claim 20, wherein said first arm is curved in a manner which defines an arc and provides a space between the first detector head that the first arm supports and the base.

23. A gamma camera according to claim 19, wherein said first arm is movable according to a movement of radial translation along the base so as to approach or move away from the axis rotation of the gramma camera.

24. A gamma camera according to claim 31, wherein said first arm is curved in a manner which defines an arc and provides a space between the first detector head that the first arm supports and the base.

25. A gamma camera according to claim 18, wherein said first arm is movable according to a movement of radial translation along the base so as to approach or move away from the axis of rotation of the gamma camera.

26. A gamma camera according to claim 18, wherein the first arm is curved in a manner which defines an arc and provides a space between the first detector head that the first arm supports and the base.

27. A gamma camera according to claim 18, wherein both fingers of each of the two-finger gripping pieces have bevelled ends.

28. A gamma camera according to claim 18, wherein the said first and said second arms are fixed to a carriage on the base and wherein a-geared motor unit supported by said carriage rotatably drives said first and second arms in angulation.

29. A gamma camera according to claim 18, wherein the second detector head is rotationally movable about a second axis called an axis of-orientation of the second detector head, said second axis of orientation being contained in a plane substantially orthogonal to the axis of angulation of the second detector head and passing through a Second position at which said second detector head is supported to the second arm.

30. A gamma camera according to claim 29, wherein the second axis of angulation of the second detector head is offset with respect to the axis of orientation of the second detector head towards a detection surface of said second head and passes substantially through the center of gravity formed by the second arm and the second head.

31. A gamma camera according to claim 18, wherein the second arm is movable according to a movement of radial translation along the base so as to approach or move away from the axis of rotation of the gamma camera.

32. A gamma camera according to claim 18, wherein the first arm and second arm are curved in a manner which defines an arc and provides a space between each of the associated first and second detector heads and the base.

33. A gamma camera according to claim 18, wherein the first detector head includes a casing having a bevelled edge adjacent a front surface thereof.

34. A gamma camera according to claim 33, wherein the second detector head includes a casing having a bevelled edge adjacent a front surface thereof.

* * * * *